US008039453B2

(12) United States Patent
Wolf et al.

(10) Patent No.: US 8,039,453 B2
(45) Date of Patent: Oct. 18, 2011

(54) VINCA DERIVATIVES

(75) Inventors: Mark A. Wolf, Delanson, NY (US); Peter R. Guzzo, Niskayuna, NY (US); Ian L Scott, Monroe, WA (US)

(73) Assignee: Albany Molecular Research, Inc., Albany, NY (US)

( * ) Notice: Subject to any disclaimer, the term of this patent is extended or adjusted under 35 U.S.C. 154(b) by 700 days.

(21) Appl. No.: 11/854,186

(22) Filed: Sep. 12, 2007

(65) Prior Publication Data

US 2008/0119502 A1    May 22, 2008

Related U.S. Application Data

(60) Provisional application No. 60/843,975, filed on Sep. 12, 2006.

(51) Int. Cl.
*A61K 31/33* (2006.01)
*C07D 487/22* (2006.01)
(52) U.S. Cl. ........................ 514/183; 540/478
(58) Field of Classification Search .................. None
See application file for complete search history.

(56) References Cited

U.S. PATENT DOCUMENTS 5,620,985 A * 4/1997 Jacquesy et al. ............. 514/283

FOREIGN PATENT DOCUMENTS

| EP | 0292463 A2 | 11/1988 |
| WO | 8605491 A1 | 9/1986 |

OTHER PUBLICATIONS

Iuchi et al. Journal of Pharmacology Sciences, 2009, 109, pp. 573-582.*
"What is arthritis? What causes arthritis", http://www.medicalnewstoday.com/articles/7621.php, Accessed Dec. 3, 2010.*
Burnham. Current Medicinal Chemistry, 2005, 12(17), 1995-2010.*
Bau et al., "Crystal Structure of Vinblastine," J. Chem. Soc. Perkin Trans. pp. 2079-2082 (2000).
Cros et al., "Experimental Antitumor Activity of Navelbine," Seminars in Oncology 16(2)(Suppl. 4):15-20 (1989).
Keuhne et al., "Syntheses and Biological Evaluation of Vinblastine Congeners," Organic and Biomolecular Chemistry 1:2120-36 (2003).
Lavoie et al., "Bioisosterism: A Rational Approach in Drug Design," Chemical Reviews 96:3147-76 (1996).
Merck Index, "Vindesine," 9982, 9986, 9987, and 9989.
Moncrief et al., "Structures of Leurocristine (Vincristine) and Vincaleukoblastine X-Ray Analysis of Leurocristine Methiodide," Journal of American Chemical Society 87(21):4963-4964 (1965).
Neuss et al., "Vinca Alkaloids XXXIII[1]. Microbiological Conversions of Vincaleukoblastine (VLB, Vinblastine), an Antitumor Alkaloid from *Vinca rosea*," Helvetica Chimica Acta 57(6):1886-90 (1974).
Sheng et al., "Synthesis and Biological Evaluation of C-12' Substituted Vinflunine Derivatives," Bioorganic & Medicinal Chemistry Letters 18:4602-4605 (2008).
Voss et al., "Synthesis and SAR of Vinca Alkaloid Analogues," Bioorganic & Medicinal Chemistry Letters 19:1245-1249 (2009).

* cited by examiner

*Primary Examiner* — Noble Jarrell
(74) *Attorney, Agent, or Firm* — LeClairRyan, a Professional Corporation

(57) ABSTRACT

The present invention relates to derivatives of vinca alkaloids. Pharmaceutical compositions containing these compounds as well as processes of preparation and treatment of various conditions are also disclosed.

41 Claims, No Drawings

VINCA DERIVATIVES

The present invention claims benefit of U.S. Provisional Application Ser. No. 60/843,975, filed Sep. 12, 2006, which is hereby incorporated by reference in its entirety.

FIELD OF THE INVENTION

The present invention relates to derivatives of the vinca alkaloids which are potent inhibitors of cellular mitosis and proliferation, as well as pharmaceutical compositions, preparation processes, and methods of use for treatment of various conditions.

BACKGROUND OF THE INVENTION

Cellular Proliferation and Cancer

The disruption of external or internal regulation of cellular growth can lead to uncontrolled cellular proliferation and in cancer, tumor formation. This loss of cellular growth control can occur at many levels and, indeed, does occur at multiple levels in most tumors. Under these circumstances, although tumor cells can no longer control their own proliferation, such cells still must use the same basic cellular machinery employed by normal cells to drive their growth and replication.

Mitosis and Spindle Formation

In a process known as mitosis, cancer cells, like all mammalian cells, multiply through replication and segregation of the original chromosomes. Following DNA replication in the S phase, the cells progress in the G2 phase. During the G2 phase, cells continue to increase in mass and prepare for mitosis. If chromosome damage is present in the G2 phase, the affected cell responds by activating the G2 phase checkpoint, which prevents progression into mitosis. In the absence of DNA damage or following repair of damage, the G2 phase cells then enter the M phase in which the identical pairs of chromosomes are separated and transported to opposite ends of the cell. The cell then undergoes division into two identical daughter cells.

In a process known as spindle formation, the cell utilizes the mitotic spindle apparatus to separate and pull apart the chromosomes. This apparatus, in part, consists of a network of microtubules that form during the first stage of mitosis. Microtubules are hollow tubes that are formed by the assembly of tubulin heterodimers from alpha- and beta-tubulin. The assembly of tubulin into microtubules is a dynamic process with tubulin molecules being constantly added and subtracted from each end.

Vinca Compounds as Inhibitors of Mitosis and Cellular Proliferation

In general, vinca compounds are known to be inhibitors of mitosis and cellular proliferation. In particular, the antiproliferative activity of the vinca alkaloid class of drugs has been shown to be due to their ability to bind tubulin. Assembly of tubulin into microtubules is essential for mitosis and the binding of the vincas to tubulin leads to cell cycle arrest in M phase and subsequently to apoptosis. For example, at low concentrations, these compounds interfere with the dynamics of microtubule formation. At higher concentrations, they cause microtubule disassembly, and at still higher concentrations, the formation of tubulin paracrystals.

Moreover, the anti-cancer activity of vinca alkaloids is generally believed to result from a disruption of microtubules resulting in mitotic arrest. However, cytotoxicity of vinca alkaloids also has been demonstrated in non-mitotic cells. Considering the role of microtubules in many cellular processes, the cytotoxic action of vinca alkaloids may involve contributions from inhibition of non-mitotic microtubule-dependent processes.

Cytotoxicity may also be a consequence of changes in membrane structure resulting from the partitioning of vinca alkaloids into the lipid bilayer. Studies with another tubulin binding compound, taxol, have shown that cell cycle arrest was not a precondition for apoptosis by agents of this type. Therefore, the anti-cancer activity of vinca alkaloids may be the result of disruption of a number of distinct microtubule-dependent and possibly microtubule-independent processes.

The assembly of tubulin into microtubules is a complex process involving dynamic instability (i.e. the switching between periods of slow growth and rapid shortening at both ends of the microtubule), and treadmilling (i.e. the addition of tubulin to one end of the microtubule occurring at the same rate as loss of tubulin from the other). Low concentrations of vinca alkaloids have been shown to bind to the ends of the microtubules and suppress both microtubule instability and treadmilling during the metaphase stage of mitosis. For example, vinca alkaloids have been shown to stabilize microtubule plus ends and destabilize microtubule minus ends. Although the spindle is retained under these conditions, there is frequently abnormal alignment of condensed chromosomes. At higher concentrations of vinca alkaloids, the spindle is not present and the chromosome distribution resembles that of prometaphase cells. At both low and high concentrations of vincas, mitotic arrest results from activation of metaphase-anaphase checkpoint. The molecular basis of this checkpoint is a negative signal sent from the kinetochore of chromosomes that are not attached to microtubules. This signal prevents the activation of pathways that result in the initiation of anaphase events.

Although there is a common binding site for the vinca alkaloids on tubulin, the members of this class do behave differently. The relative overall affinities for β-tubulin binding are vincristine>vinblastine>vinorelbine>vinflunine, but there is no significant difference in the affinity of all four drugs for tubulin heterodimers. The discrepancy has primarily been explained by differences in the affinities of vinca-bound heterodimers for spiral polymers and the binding of drug to unliganded polymers. For example, tubulin spirals induced by vinflunine are significantly smaller than those induced by vinorelbine.

In addition, vinca alkaloids also differ in their effects on microtubule dynamics. Vinflunine and vinorelbine suppress dynamic instability through: slowing the microtubule growth rate, increasing the mean duration of a growth event and reducing the duration of shortening. In contrast, vinblastine reduces the rate of shortening and increases the percentage of time the microtubules spend in the attenuated state. Vinblastine, vinorelbine, and vinflunine all suppress treadmilling, with vinblastine displaying the greatest potency.

In Vivo Properties

The vinca derivatives fall into the general class of cytotoxic anti-cancer agents and, as such, suffer from the same problem as all cytotoxics—i.e., toxicity. Vincristine and vinblastine are neurotoxic. Vinorelbine, which is structurally very similar to vinblastine and vincristine and is only slightly less potent, is less neurotoxic. This change in toxicity cannot be explained by examination of the binding affinity of these compounds for tubulin alone. It has been postulated to arise from an increase in sensitivity to changes in microtubule dynamics in tumor cells and, as described above, these compounds have been shown to have subtly different effects. It could also arise from changes in cellular uptake of the drug. Vinflunine is not very potent in vitro yet is active in vivo, and this has been attributed to its superior cellular uptake. There are also quite significant differences in the profile of efficacy of vinca alkaloids. Vincristine has found wide use in the treatment of hematologic malignancies including leukemias and lymphomas. It is also widely used in pediatric solid tumors and, in the past, in small cell lung cancer. Vinblastine is an important component of the combination regimen that is curative for testicular cancer. Vinorelbine is quite different and has found use mainly in breast cancer and non-small cell lung cancer.

There remains a need for novel vinca derivatives with improved pharmacological and therapeutic properties, improved processes for the preparations of such vinca derivative compounds, corresponding pharmaceutical compositions, and methods of use.

The present invention is directed to achieving these objectives.

SUMMARY OF THE INVENTION

The present invention relates to a compound of Formula (I) as follows:

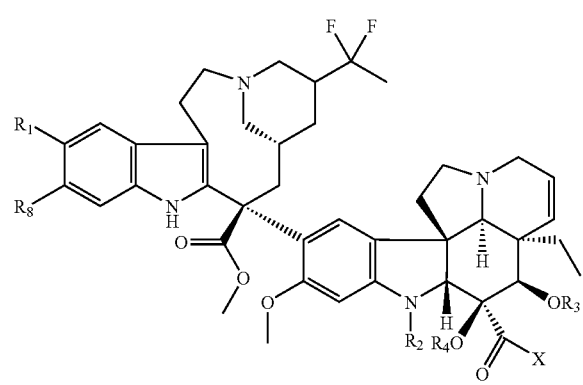

Formula I where:
$R_1$ is:
  alkyl;
  alkenyl;
  alkynyl;
  aryl;
  heterocyclyl;
  halogen;
  CN;
  CH(O);
  $COR_5$;
  $C(O)NHR_5$;
  $C(O)NR_5R_6$;
  $C(S)NH_2$;
  $C(O)NHNH_2$;
  $C(O)NR_5NH_2$;
  $C(O)NR_5NHR_6$;
  $C(O)NR_5NR_6R_7$;
  $C(O)NHNHR_5$;
  $C(O)NHNR_5R_6$;
  C(O)NHOH;
  $SO_2NHNH_2$;
  $SO_2NR_5NH_2$;
  $SO_2NR_5NHR_6$;
  $SO_2NR_5NR_6R_7$;
  $SO_2NHNHR_5$;
  $SO_2NHNR_5R_6$;
  $CO_2R_5$;
  $SR_5$;
  $SSR_5$;
  $SO_2NHR_5$;
  $SO_2NR_5R_6$;
  $B(OR_5)_2$;
  $CF_3$;
  SH;
  $SO_2NH_2$;
  $NH_2$;
  $NHR_5$;
  $NHSO_2R_5$;
  $NR_5R_6$;
  $NHCOR_5$;
  $NR_5COR_6$;
  $NR_5SO_2R_6$;
  $SOR_5$;
  $SO_2R_5$;
  $OR_9$; or
$R_2$=alkyl or CH(O);
$R_3$=hydrogen, alkyl, or $C(O)R_5$;
$R_4$=hydrogen or $C(O)R_5$;
$R_5$, $R_6$, and $R_7$ each are independently hydrogen, alkyl, alkenyl, alkynyl, aryl, or heterocyclyl;
$R_8$=hydrogen, halogen, alkyl, alkenyl, alkynyl, aryl, heterocyclyl, acyl, or thioalkyl;
$R_5$ and $R_6$ could form a ring as could $R_6$ and $R_7$.
X=$OR_5$, $NR_5R_6$, $NHNH_2$, $NHNHC(O)R_5$, OH, $NHR_5$, $NH_2$, or NHNHC(O)H;
$R_4$ and X may be linked together with intervening atoms to form a ring; $R_1$ and $R_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted.

Another compound in accordance with the present invention is the compound of Formula II as follows:

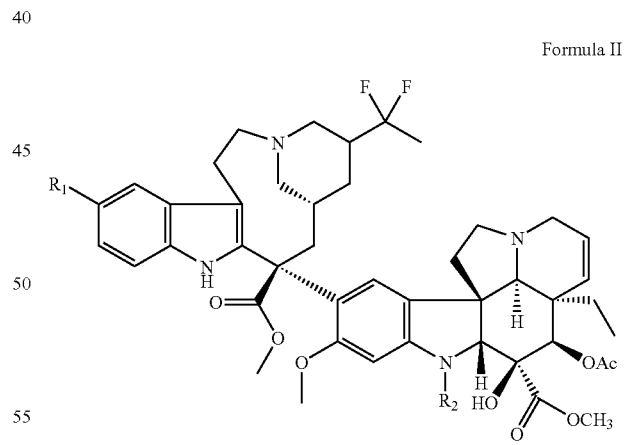

Formula II where:
$R_1$ is
  alkyl;
  alkenyl;
  alkynyl;
  CN;
  $SR_5$;
  $CF_3$;
  $OR_7$;

$R_2$=alkyl or CH(O);

$R_5$ and $R_7$ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

A further compound of the present invention is the compound of Formula III as follows:

Formula III where:

$R_1$ is:
  alkyl;
  $SR_5$;
  $OR_7$;

$R_5$ and $R_7$ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

The compound of Formula IV is another compound in accordance with the present invention:

Formula IV where:

$R_1$ is alkyl; or a pharmaceutically acceptable salt thereof, wherein the alkyl group may be branched, straight, unsubstituted, and/or substituted.

An additional compound in accordance with the present invention is the compound of Formula V as follows:

Formula V where:

$R_5$=alkyl; or a pharmaceutically acceptable salt thereof, wherein the alkyl group may be branched, straight, unsubstituted, and/or substituted.

Another aspect of the present invention relates to a process for preparation of a derivative product compound of Formula (I) as follows:

Formula I where:

$R_1$ is:
  alkyl;
  alkenyl;
  alkynyl;
  aryl;
  heterocyclyl;
  CN;
  CH(O);
  $COR_5$;
  $C(O)NR_5R_6$;
  $C(O)NHR_5$;
  $C(O)NH_2$;
  $C(O)NHNH_2$;
  $C(O)NR_5NH_2$;
  $C(O)NR_5NHR_6$;
  $C(O)NR_5NR_6R_7$;
  $C(O)NHNHR_5$;
  $C(O)NHNR_5R_6$;
  C(O)NHOH;

SO$_2$NHNH$_2$;
SO$_2$NR$_5$NH$_2$;
SO$_2$NR$_5$NHR$_6$;
SO$_2$NR$_5$NR$_6$R$_7$;
SO$_2$NHNHR$_5$;
SO$_2$NHNR$_5$R$_6$;
CO$_2$R$_5$;
SR$_5$;
SSR$_5$;
SO$_2$NHR$_5$;
SO$_2$NR$_5$R$_6$;
B(OR$_5$)$_2$;
CF$_3$;
SH;
SO$_2$NH$_2$;
NH$_2$;
NHR$_5$;
NHCOR$_5$;
NHSO$_2$R$_5$;
NR$_5$R$_6$;
NHCOR$_5$;
NR$_5$COR$_6$; or
NR$_5$SO$_2$R$_6$;
SOR$_5$;
SO$_2$R$_5$;
OR$_7$; or

R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ could form a ring or R$_6$ and R$_7$ could form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; R$_1$ and R$_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. The process involves converting an intermediate compound of formula:

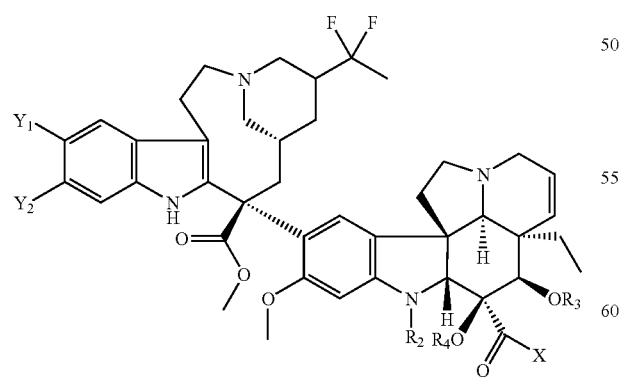

where Y$_1$ is a halogen and Y$_2$ is halogen or hydrogen, under conditions effective to produce the product compound of Formula (I).

Another aspect of the present invention relates to a process for preparation of a derivative product compound of Formula (I) as follows:

Formula I

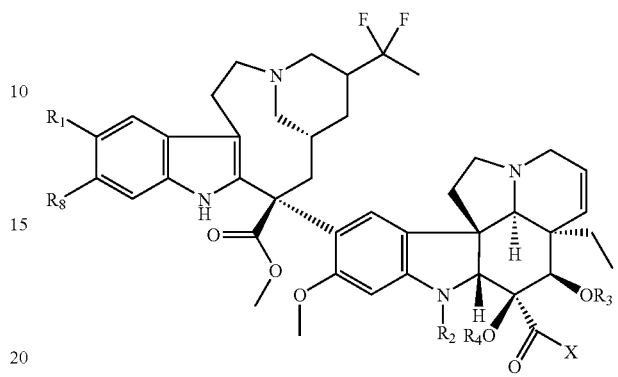

where:
R$_1$=halogen;
R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ could form a ring or R$_6$ and R$_7$ could form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; R$_1$ and R$_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. The process involves halogenating a starting material of the formula:

under conditions effective to form the derivative product compound.

Another aspect of the present invention relates to a process for preparation of a derivative product compound of Formula (I) as follows:

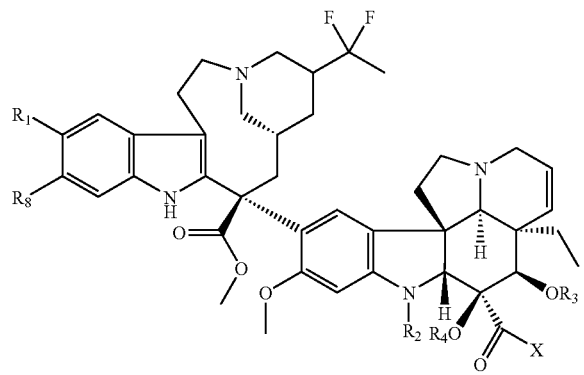

Formula I where:
R$_1$ is:
  alkyl;
  alkenyl;
  alkynyl;
  aryl;
  heterocyclyl;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHCOR$_5$;
  NHSO$_2$R$_5$;
  NR$_5$R$_6$;
  NHCOR$_5$;
  NR$_5$COR$_6$;
  NR$_5$SO$_2$R$_6$;
  SOR$_5$;
  SO$_2$R$_5$; or
  OR$_7$;

R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ can form a ring or R$_6$ and R$_7$ can form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; R$_1$ and R$_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. This process involves fluorinating an intermediate compound of formula:

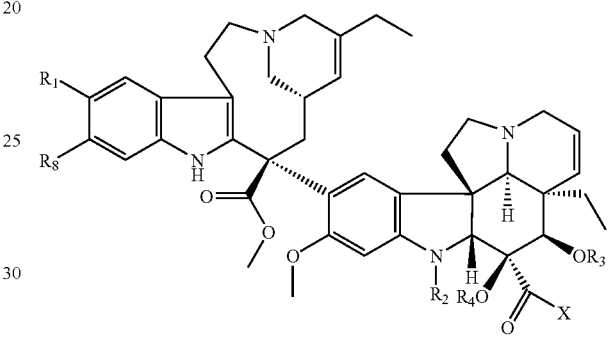

under conditions effective to produce the product compound of Formula (I).

The present invention also relates to a method for inhibiting cell proliferation in mammals, which comprises administering a therapeutically effective amount of the compound of Formula (I) to the mammal.

The present invention also relates to a method for treating a condition in mammals, which comprises administering a therapeutically effective amount of the compound of Formula (I) to the mammal. The condition can be bacterial infection, allergy, heart disease, AIDS, Human T-lymphotropic virus 1 infection, Human herpesvirus 3, Human herpesvirus 4, Human papillomavirus, diabetes mellitus, rheumatoid arthritis, Alzheimer's Disease, inflammation, arthritis, asthma, malaria, autoimmune disease, eczema, Lupus erythematosus, psoriasis, rheumatic diseases, Sjogren's syndrome, and viral infection.

The present invention also relates to a pharmaceutical composition of matter, which comprises the compound of Formula (I) and one or more pharmaceutical excipients.

DETAILED DESCRIPTION OF THE INVENTION

The present invention relates to novel derivatives of the vinca alkaloids, corresponding pharmaceutical compositions, preparation processes, and methods of use for treatment of various diseases.

In general, the novel compounds of the vinca family of compounds of the present invention, include derivatives of vincristine, vinblastine, anhydrovinblastine, and anhydrovincristine, etc. In accordance with the present invention, such derivative compounds are represented by the chemical structure of Formula (I) as shown herein.

In particular, the present invention relates to a compound of Formula (I) as follows:

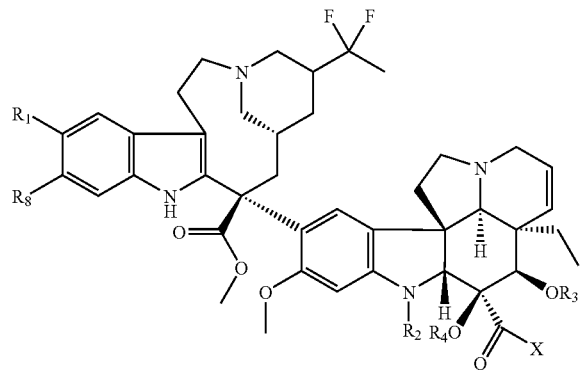

Formula I where:
R$_1$=alkyl;
  alkenyl;
  alkynyl;
  aryl;
  heterocyclyl;
  halogen;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHSO$_2$R$_5$;
  NR$_5$R$_6$;
  NHCOR$_5$;
  NR$_5$COR$_6$;
  NR$_5$SO$_2$R$_6$;
  SOR$_5$;
  SO$_2$R$_5$; or
  OR$_7$;

R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ could form a ring or R$_6$ and R$_7$ could form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. As used above, and throughout the description of the invention, the following terms, unless otherwise indicated, shall be understood to have the following meanings:

The term "heterocyclyl" means the prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. Representative monocyclic aromatic heterocycles include pyrrole, pyridine, oxazole, thiazole and the like. Representative monocyclic non-aromatic heterocycles include pyrrolidine, piperidine, piperazine and the like.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "halogen" means fluoro, chloro, bromo, or iodo.

The term term "thioalkyl" means sulfur bonded to an alkyl group to give a thioether.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

In one embodiment, the present invention relates to a compound where $R_3$=acetyl.

In another embodiment, the present invention relates to a compound where $R_4$=hydrogen.

In another embodiment, the present invention relates to a compound where X=OMe.

In another embodiment, the present invention relates to a compound where $R_3$=acetyl, $R_4$=hydrogen, and X=OMe.

In another embodiment, the present invention relates to a compound where $R_2$=CH(O).

In another embodiment, the present invention relates to a compound where $R_2$=alkyl.

Representative examples of the compounds of Formula (I) are set forth in Table 1 below:

TABLE 1

| Compounds of Formula (I) | | |
| --- | --- | --- |
| Example Number | COMPOUND OF FORMULA (I) | NAME OF VINCA COMPOUND |
| 1 | | 12'-Bromo-4'-deoxy-20',20'-diflurovincaleukoblastine |
| 2 | | 12'-Iodo-4'-deoxy-20',20'-diflurovincaleukoblastine |
| 3 | | 12'-Ethyl-4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 4 | | 12'-Vinyl-4'-deoxy-20',20'-diflurovincaleukoblastine |
| 5 | | 12'-Ethynyl-4'-deoxy-20',20'-diflurovincaleukoblastine |
| 6 | | 12'-Phenyl-4'-deoxy-20',20'-diflurovincaleukoblastine |
| 7 | | 12'-(4-Pyridyl)-4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 8 | | 12'-Cyano-4'-deoxy-20',20'-diflurovincaleukoblastine |
| 9 | | 12'-Formyl-4'-deoxy-20',20'-diflurovincaleukoblastine |
| 10 | | 12'-Acetyl-4'-deoxy-20',20'-diflurovincaleukoblastine |
| 11 | | 12'-(Methoxycarbonyl)-4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 12 | | 12'-(Methylsulfanyl)-4'-deoxy-20',20'-diflurovincaleukoblastine |
| 13 | | 12'-Methyl-4'-deoxy-20',20'-diflurovincaleukoblastine |
| 14 | | 12'-Isopropyl-4'-deoxy-20',20'-diflurovincaleukoblastine |
| 15 | | 12'-(Ethylsulfanyl)-4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 16 | | 12'-(Methylsulfinyl)-4'-deoxy-20',20'-diflurovincaleukoblastine |
| 17 | | 12'-(Methylsulfonyl)-4'-deoxy-20',20'-diflurovincaleukoblastine |
| 18 | | 12'-(N-Methylsulfonamido)-4'-deoxy-20',20'-diflurovincaleukoblastine |
| 19 | | 12'-(N,N-Dimethylsulfonamido) 4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 20 | | 12'-Trifluoromethyl-4'-deoxy-20',20'-diflurovincaleukoblastine |
| 21 | | 12'-Amino-4'-deoxy-20',20'-diflurovincaleukoblastine |
| 22 | | 12'-Acetamido-4'-deoxy-20',20'-diflurovincaleukoblastine |

TABLE 1-continued

Compounds of Formula (I)

| Example Number | COMPOUND OF FORMULA (I) | NAME OF VINCA COMPOUND |
|---|---|---|
| 23 | | 12'-(Methanesulfonamido)-4'-deoxy-20',20'-diflurovincaleukoblastine |
| 24 | | 12'-(N,N-Dimethylamino)-4'-deoxy-20',20'-diflurovincaleukoblastine |
| 25 | | 12'-(Pyrrolin-1-yl)-4'-deoxy-20',20'-diflurovincaleukoblastine |
| 26 | | 12'-Methoxy-4'-deoxy-20',20'-diflurovincaleukoblastine |

In yet another embodiment of the present invention, a complex can be formed which includes 2 structures of Formula (I) joined together at their $R_1$ groups, where each $R_1$ is —S—.

Another compound in accordance with the present invention is the compound of Formula II as follows:

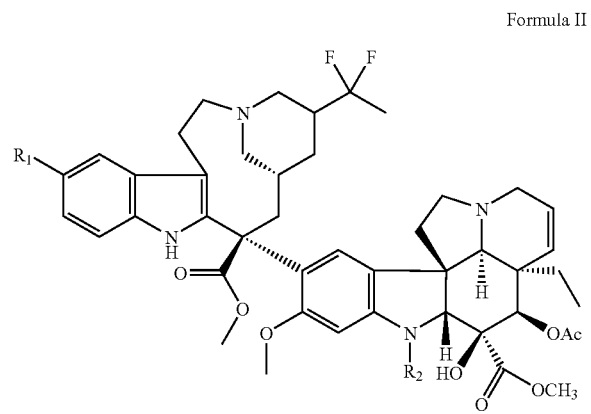

Formula II where:
$R_1$ is
  alkyl;
  alkenyl;
  alkynyl;
  CN;
  $SR_5$;
  $CF_3$;
  $OR_7$;
$R_2$=alkyl or CH(O);
$R_5$ and $R_7$ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

A further compound of the present invention is the compound of Formula III as follows:

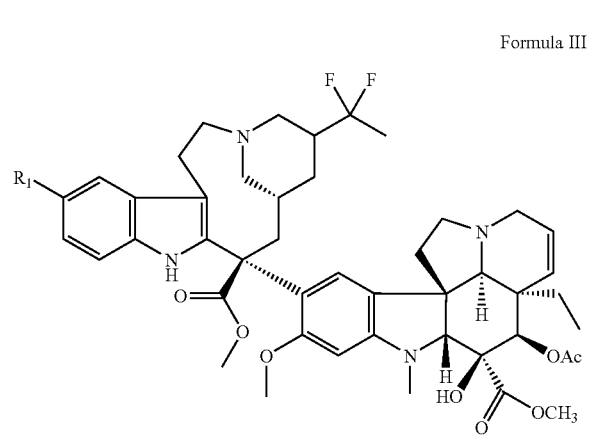

Formula III where:
$R_1$ is:
  alkyl;
  $SR_5$;
  $OR_7$;

$R_5$ and $R_7$ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

The compound of Formula IV is another compound in accordance with the present invention:

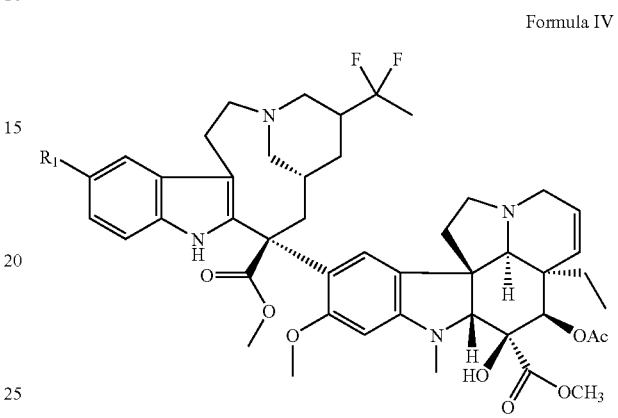

Formula IV where:

$R_1$ is alkyl; or a pharmaceutically acceptable salt thereof, wherein the alkyl group may be branched, straight, unsubstituted, and/or substituted.

The following are example of the compound of Formula IV:

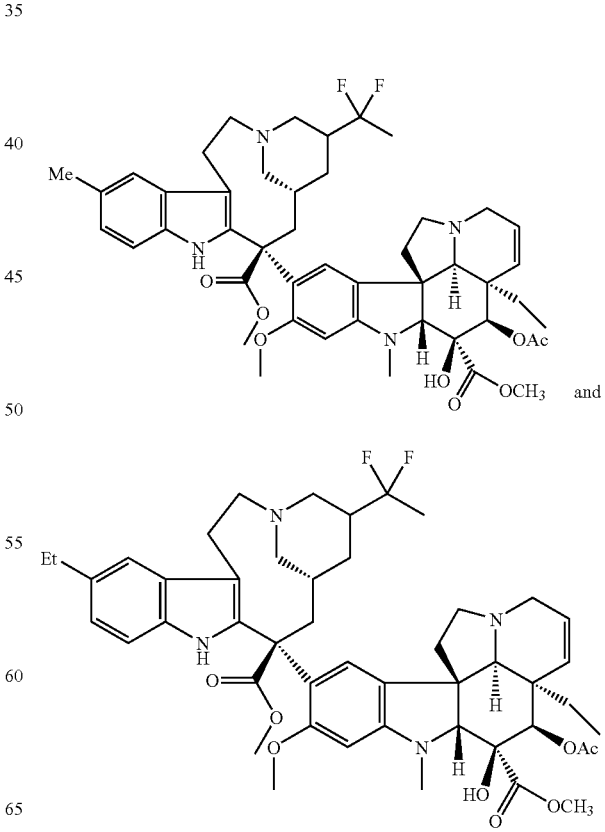

An additional compound in accordance with the present invention is the compound of Formula V as follows:

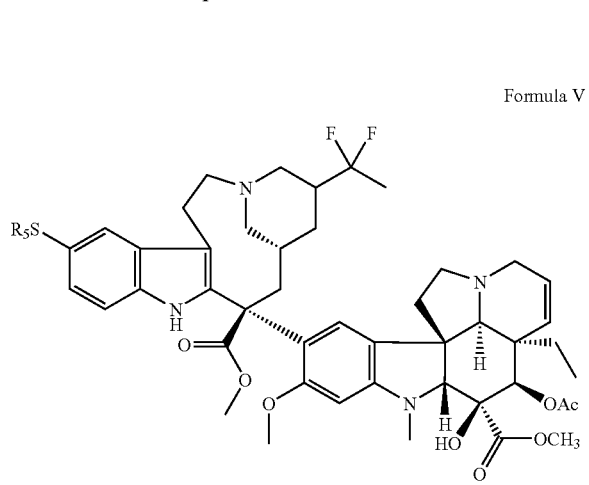

Formula V where:
$R_5$=alkyl; or a pharmaceutically acceptable salt thereof, wherein the alkyl group may be branched, straight, unsubstituted, and/or substituted.

The following are example of the compound of Formula V:

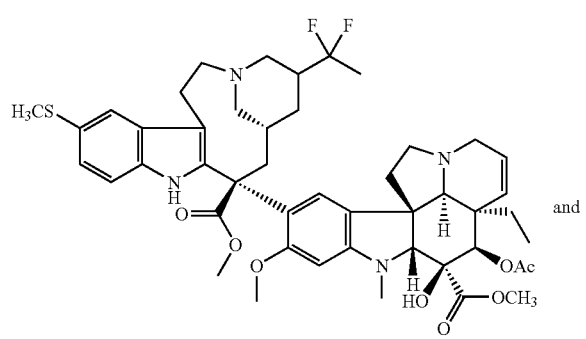

and

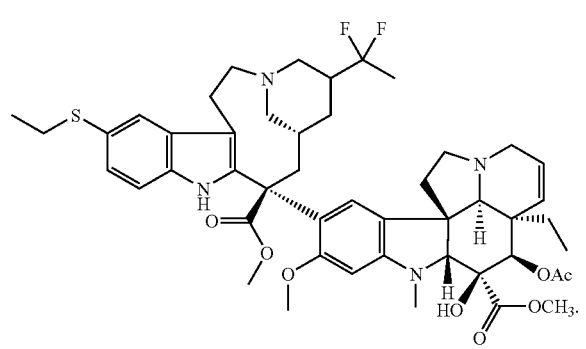

Another aspect of the present invention relates to a process for preparation of a derivative product compound of Formula (I) as follows:

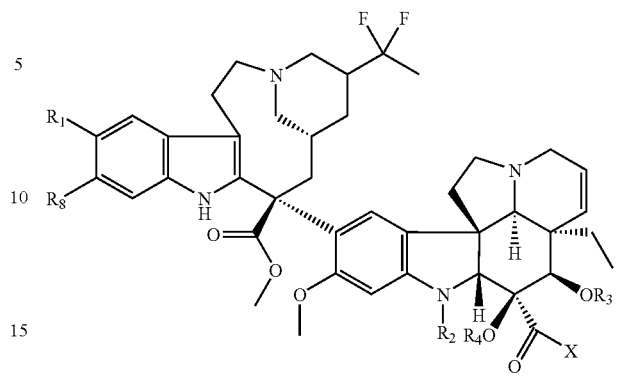

Formula I where:
$R_1$ is:
  alkyl;
  alkenyl;
  alkynyl;
  aryl;
  heterocyclyl;
  CN;
  CH(O);
  $COR_5$;
  $C(O)NR_5R_6$;
  $C(O)NHR_5$;
  $C(O)NH_2$;
  $C(O)NHNH_2$;
  $C(O)NR_5NH_2$;
  $C(O)NR_5NHR_6$;
  $C(O)NR_5NR_6R_7$;
  $C(O)NHNHR_5$;
  $C(O)NHNR_5R_6$;
  C(O)NHOH;
  $SO_2NHNH_2$;
  $SO_2NR_5NH_2$;
  $SO_2NR_5NHR_6$;
  $SO_2NR_5NR_6R_7$;
  $SO_2NHNHR_5$;
  $SO_2NHNR_5R_6$;
  $CO_2R_5$;
  $SR_5$;
  $SSR_5$;
  $SO_2NHR_5$;
  $SO_2NR_5R_6$;
  $B(OR_5)_2$;
  $CF_3$;
  SH;
  $SO_2NH_2$;
  $NH_2$;
  $NHR_5$;
  $NHCOR_5$;
  $NHSO_2R_5$;
  $NR_5R_6$;
  $NHCOR_5$;
  $NR_5COR_6$; or
  $NR_5SO_2R_6$;
  $SOR_5$;
  $SO_2R_5$;
  $OR_7$; or
$R_2$=alkyl or CH(O);
$R_3$=hydrogen, alkyl, or $C(O)R_5$;
$R_4$=hydrogen or $C(O)R_5$;

$R_5$, $R_6$, and $R_7$ each are independently hydrogen, alkyl, alkenyl, alkynyl, aryl, or heterocyclyl;

$R_8$=hydrogen, halogen, alkyl, alkenyl, alkynyl, aryl, heterocyclyl, acyl, or thioalkyl;

$R_5$ and $R_6$ could form a ring or $R_6$ and $R_7$ could form a ring;

X=$OR_5$, $NR_5R_6$, $NHNH_2$, $NHNHC(O)R_5$, OH, $NHR_5$, $NH_2$, or NHNHC(O)H;

$R_4$ and X may be linked together with intervening atoms to form a ring; $R_1$ and $R_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. The process involves converting an intermediate compound of formula:

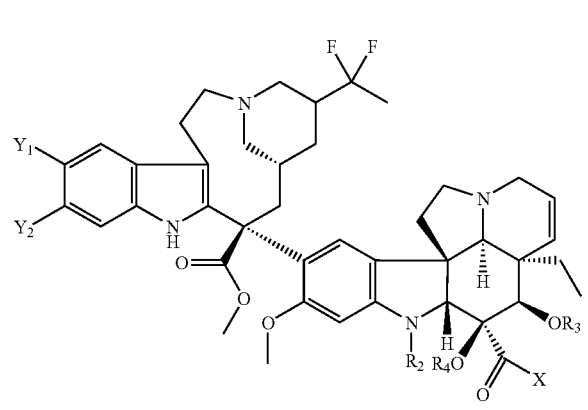

where $Y_1$ is a halogen and $Y_2$ is halogen or hydrogen, under conditions effective to produce the product compound of Formula (I).

The intermediate compound is formed by reacting a starting material compound of the formula:

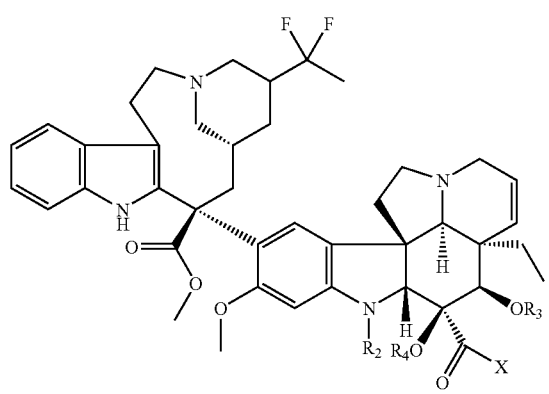

under conditions effective to form the intermediate compound.

Another aspect of the present invention relates to a process for preparation of a derivative product compound of Formula (I) as follows:

Formula I

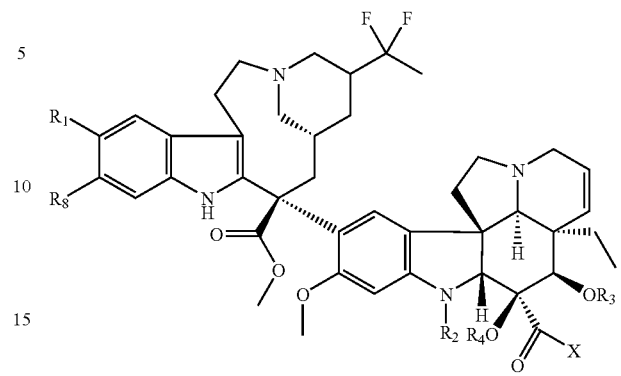

where:

$R_1$=halogen;

$R_2$=alkyl or CH(O);

$R_3$=hydrogen, alkyl, or $C(O)R_5$;

$R_4$=hydrogen or $C(O)R_5$;

$R_5$, $R_6$, and $R_7$ each are independently hydrogen, alkyl, alkenyl, alkynyl, aryl, or heterocyclyl;

$R_8$=hydrogen, halogen, alkyl, alkenyl, alkynyl, aryl, heterocyclyl, acyl, or thioalkyl;

$R_5$ and $R_6$ could form a ring or $R_6$ and $R_7$ could form a ring;

X=$OR_5$, $NR_5R_6$, $NHNH_2$, $NHNHC(O)R_5$, OH, $NHR_5$, $NH_2$, or NHNHC(O)H;

$R_4$ and X may be linked together with intervening atoms to form a ring; $R_1$ and $R_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. The process involves halogenating a starting material of the formula:

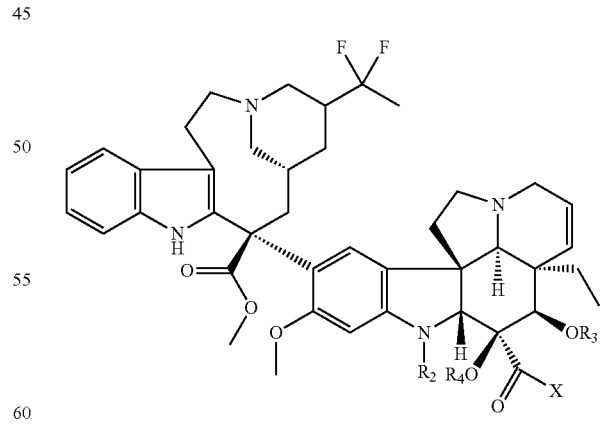

under conditions effective to form the derivative product compound.

Another aspect of the present invention relates to a process for preparation of a derivative product compound of Formula (I) as follows:

Formula I

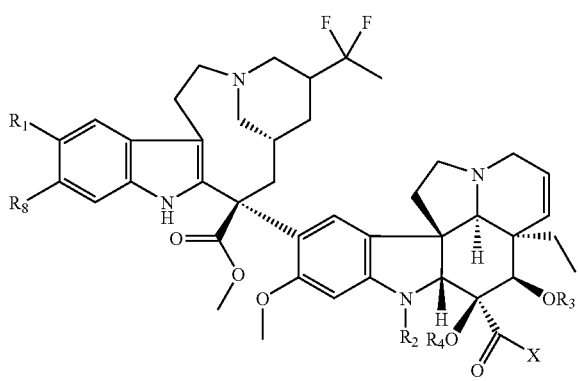

where:
R$_1$ is:
  alkyl;
  alkenyl;
  alkynyl;
  aryl;
  heterocyclyl;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHCOR$_5$;
  NHSO$_2$R$_5$;
  NR$_5$R$_6$;
  NHCOR$_5$;
  NR$_5$COR$_6$;
  NR$_5$SO$_2$R$_6$;
  SOR$_5$;
  SO$_2$R$_5$; or
  OR$_7$;

R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ can form a ring or R$_6$ and R$_7$ can form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; R$_1$ and R$_8$ may be linked together; or a pharmaceutically acceptable salt thereof, where the alkyl and alkenyl groups may be branched, straight, unsubstituted, and/or substituted and where the aryl, alkynyl, and heterocyclyl groups are substituted or unsubstituted. This process involves fluorinating an intermediate compound of formula:

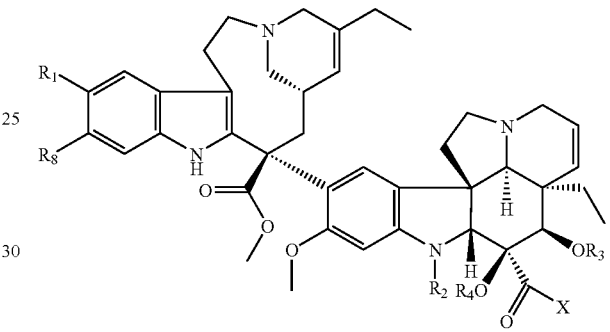

under conditions effective to produce the product compound of Formula (I).

The intermediate compound is formed by converting a starting material compound of formula:

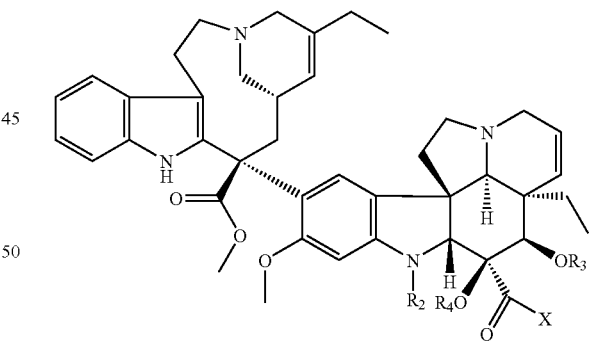

under conditions effective to form the intermediate compound.

A synthetic scheme for preparing compounds of Formula (I) is shown in Scheme 1 below. A vinca alkaloid is treated with either N-bromosuccinimide or N-iodosuccinimide to introduce halogens in the 12' and 13'-positions. Pd-mediated coupling is then used to introduce other functionality at these position. This methodology can be used to introduce alkyl, alkenyl, alkynyl, aryl, heterocyclyl, acyl, cyano, amino, and formyl groups and to form sulphides. Each of these groups can then be subjected to further derivatization following standard methods of organic synthesis.

Scheme 1

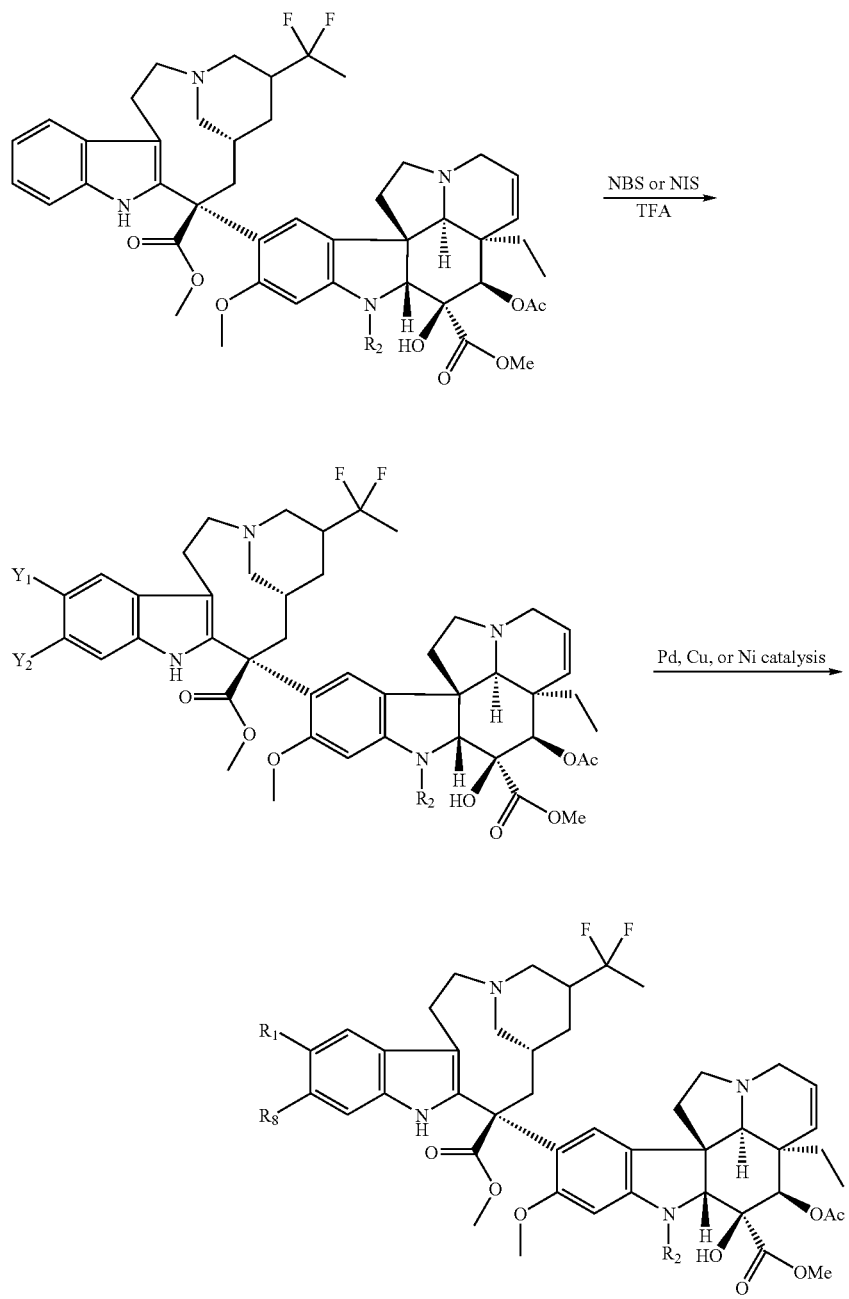

Y = Br, I
R₂ = Me, CHO
R₁, R₈ = previously defined list herein
NBS = N-Bromosuccinimide
NIS = N-Iodosuccinimide In practicing the above process, a variety of catalysts may be utilized, such as palladium chloride, palladium acetate, tris(dibenzylideneacetone)palladium(0), tetrakis(triphenylphosphine)palladium(0), dichlorobis(triphenylphosphine)palladium(II), benzylchlorobis(triphenylphosphine)palladium(II), or [1,1'-bis(diphenylphosphino)ferrocene]dichloropalladium(II).

Scheme 2 below outlines an alternative synthesis of these analogs starting from anhydrovinblastine.

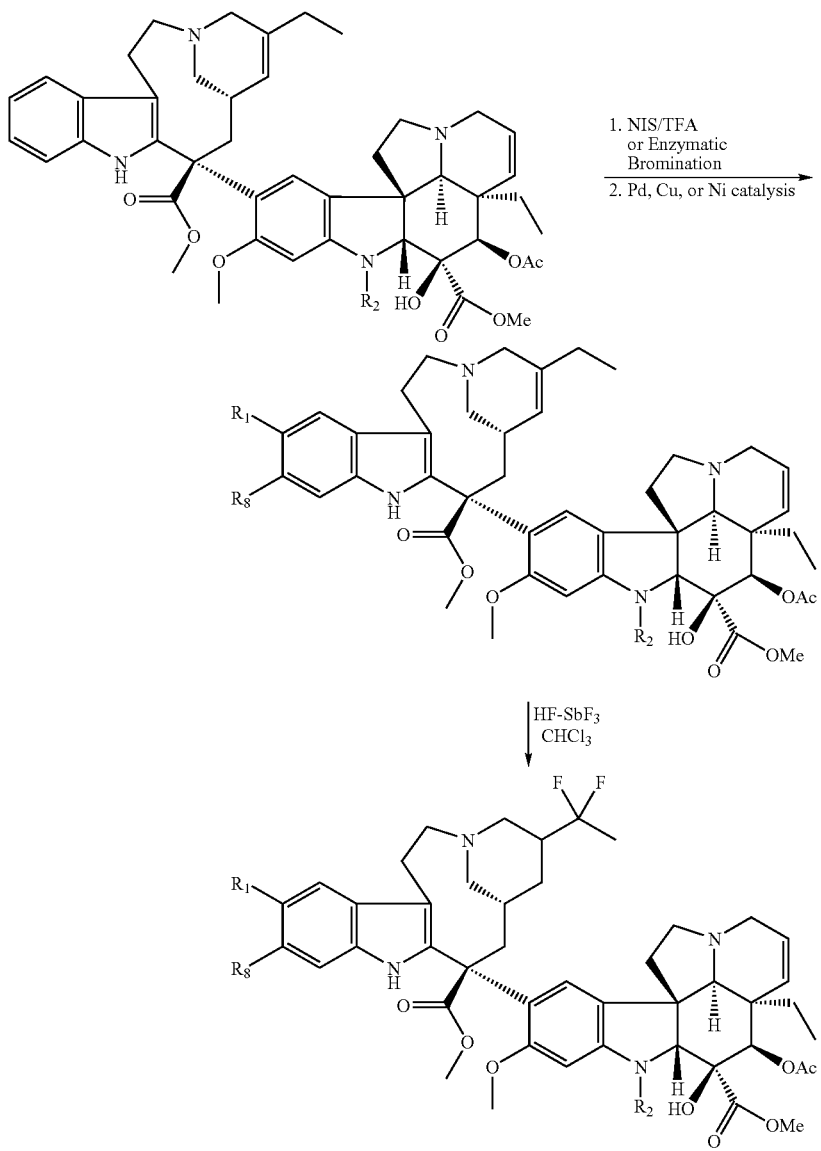

Scheme 2

$R_2$ = Me, CHO
$R_1$, $R_8$ = previously defined list herein
NBS = N-Bromosuccinimide
NIS = N-Iodosuccinimide The compounds of the present invention are useful in inhibiting cellular proliferation in a mammal by administering to such mammal an effective amount of compound(s) of the present invention.

In particular, such vinca compound derivatives are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, (e.g., sarcomas), carcinomas, (e.g., astrocytomas), lymphomas, (e.g., adult T-cell lymphoma), different cancer disease types, (e.g., prostate cancer, breast cancer, small cell lung cancer, ovarian cancer), Hodgkin's Disease, and other neoplastic disease states (e.g., leukemias, particularly adult T-cell leukemias).

Since vinca compounds are known to be tubulin inhibitors, the compounds of the present invention would also be expected to be useful in treating the following conditions: bacterial infection; allergy; heart disease; AIDS; Human T-lymphotropic virus 1 infection; Human herpesvirus 3; Human herpesvirus 4; Human papillomavirus; diabetes mellitus; rheumatoid arthritis; Alzheimer's Disease; inflammation; arthritis; asthma; malaria; autoimmune disease; eczema; Lupus erythematosus; psoriasis; rheumatic diseases; Sjogren's syndrome; and viral infection.

The vinca derivative compounds of the present invention can be administered alone, as indicated above, or utilized as biologically active components in pharmaceutical compositions with suitable pharmaceutically acceptable carriers, adjuvants and/or excipients.

In accordance with the present invention, the compounds and/or corresponding compositions can be introduced via different administration routes, which include orally, parenterally, intravenously, intraperitoneally, by intranasal instillation, or by application to mucous membranes, such as, that of the nose, throat, and bronchial tubes.

The active compounds of the present invention may be orally administered, for example, with an inert diluent, or with an assimilable edible carrier, or they may be enclosed in hard or soft shell capsules, or they may be compressed into tablets.

The quantity of the compound administered will vary depending on the patient and the mode of administration and can be any effective amount. The quantity of the compound administered may vary over a wide range to provide in a unit dosage an effective amount of from about 0.01 to 20 mg/kg of body weight of the patient per day to achieve the desired effect. The amount of active compound in such therapeutically useful compositions is such that a suitable dosage will be obtained. Preferred compositions according to the present invention are prepared so that an oral dosage unit contains between about 1 and 250 mg of active compound.

For example, with oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both.

These active compounds and/or pharmaceutical compositions may also be administered parenterally. Solutions of these active compounds and/or compositions can be prepared in water. Dispersions can also be prepared in glycerol, liquid polyethylene glycols, and mixtures thereof in oils.

Illustrative oils are those of animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the pharmaceutical form of the present invention must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds and/or pharmaceutical compositions of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Some of the compounds of the present invention can be in the form of pharmaceutically acceptable acid-addition and/or base salts. All of these forms of salts are within the scope of the present invention.

Pharmaceutically acceptable acid addition salts of the compounds of the present invention include salts derived from nontoxic inorganic acids, such as hydrochloric acid, nitric acid, phosphoric acid, sulfuric acid, hydrobromic acid, hydroiodic acid, hydrofluoric acid, phosphorous acid, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety).

The acid addition salts of said basic compounds are prepared by contacting the free base forms with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenedianline, N-methylglucamine, and procaine (see, for example, Berge S. M. et al., "Pharmaceutical Salts," *Journal of Pharmaceutical Science*, 66:1-19 (1997), which is hereby incorporated by reference in its entirety).

The base addition salts of the acidic compounds are prepared by contacting the free acid form with a sufficient amount of the desired base to produce the salt in the conventional mariner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The present invention can be used in conjunction with other know cancer treatments, including other chemotherapeutic agents and radiation.

EXAMPLES

Experimental Introduction

Unless otherwise noted, reagents and solvents were used as received from commercial suppliers. Purifications using the notation 'column' were carried out on an automated Combiflash unit consisting of a gradient mixing system, Foxy 200 fraction collector and a UV/visible detector. Proton and carbon nuclear magnetic resonance spectra were obtained on a Bruker AC 300 or a Bruker AV 300 spectrometer at 300 MHz for proton and 75 MHz for carbon, or on a Bruker AMX 500 spectrometer at 500 MHz for proton and 125 MHz for carbon. Spectra are given in ppm (δ) and coupling constants, J, are reported in Hertz. Tetramethylsilane was used as an internal standard for proton spectra and the solvent peak was used as the reference peak for carbon spectra. Mass spectra were obtained on a Finnigan LCQ Duo LCMS ion trap electrospray ionization (ESI) mass spectrometer. HPLC analyses were obtained using a Luna C18(2) column (250×4.6 mm, Phenomenex) with UV detection at 223 or 254 nm using a standard solvent gradient program (Method A). Liquid chromatography-mass spectrometry was obtained on a Varian 1200L single quadrapole mass spectrometer using ESI and a Luna C18(2) column (50×4.6 mm, Phenomenex) with UV detection at 223 or 254 nm using a standard solvent gradient program (Method B).

| Method A: | | | | Method B: | | | |
|---|---|---|---|---|---|---|---|
| Time (min) | Flow (mL/min) | % A | % B | Time (min) | Flow (mL/min) | % A | % B |
| 0.0 | 1.0 | 90.0 | 10.0 | 0.0 | 2.5 | 90.0 | 10.0 |
| 20 | 1.0 | 0.0 | 100.0 | 4 | 2.5 | 0.0 | 100.0 |
| 30 | 1.0 | 0.0 | 100.0 | 6 | 2.5 | 0.0 | 100.0 |
| 35 | 1.0 | 90.0 | 10.0 | 7 | 2.5 | 90.0 | 10.0 |

A = 100% Water with 0.025% or 0.05% v/v Trifluoroacetic Acid
B = 100% Acetonitrile, 0.025% or 0.05% v/v Trifluoroacetic Acid Compounds in accordance with the present invention were synthesized pursuant to Scheme 3 as follows:

Scheme 3

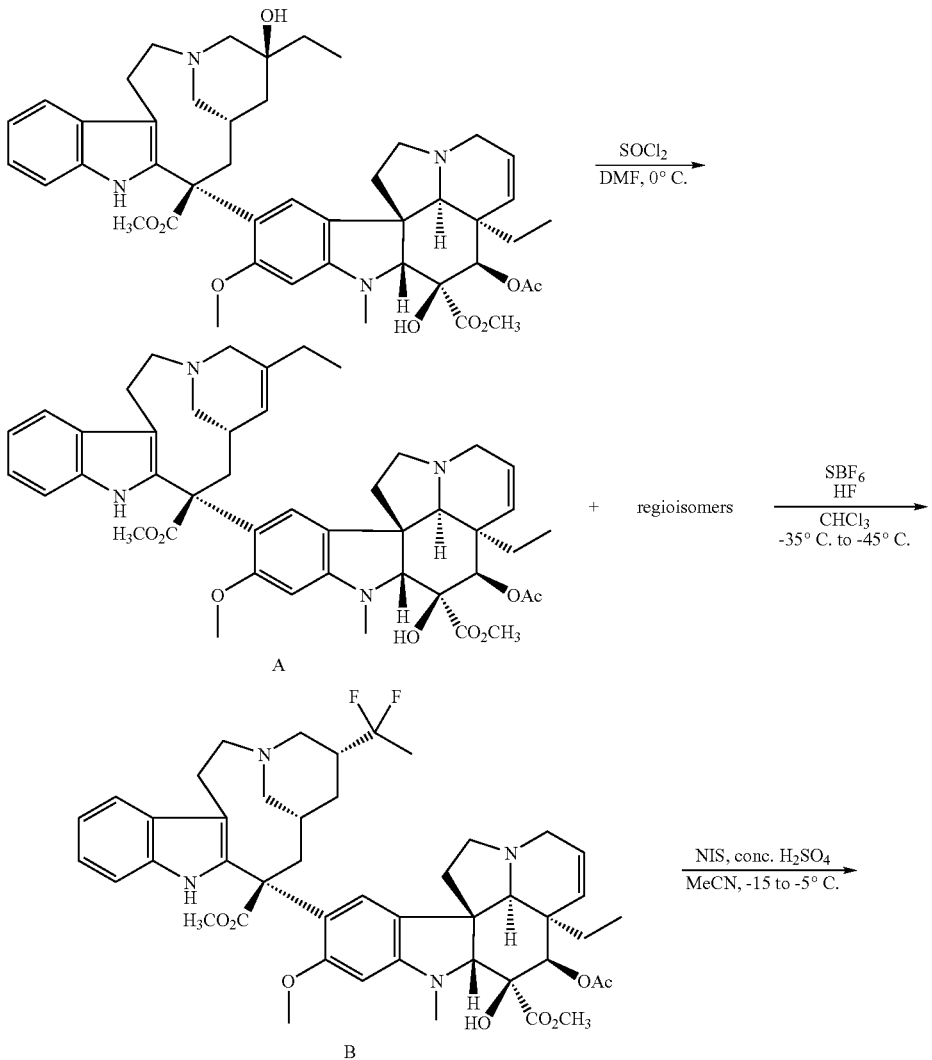

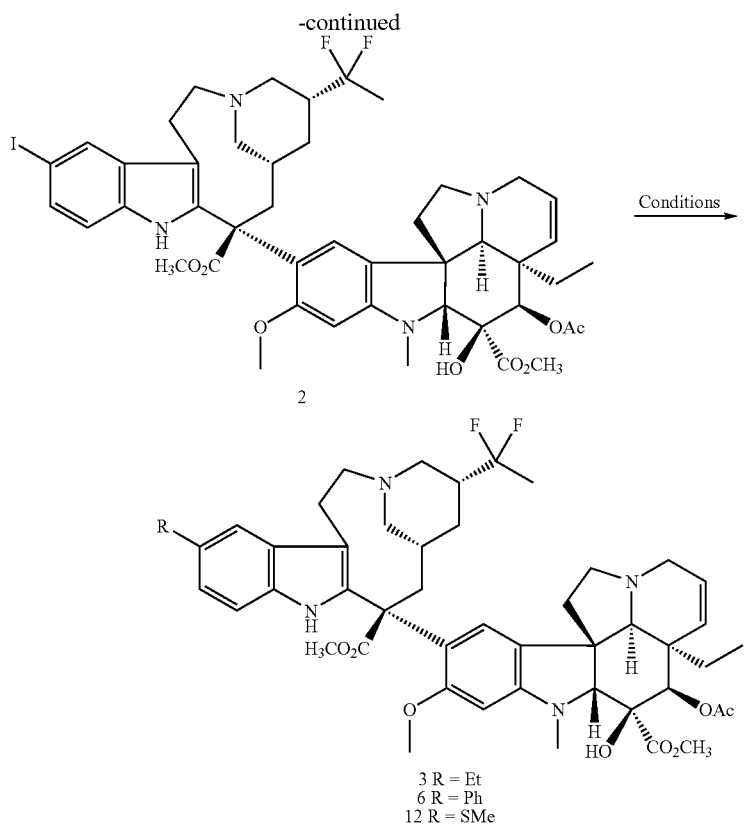

3 R = Et
6 R = Ph
12 R = SMe

Conditions: a. MeSH, Pd(dppf)Cl₂, Et₃N, NMP, 50-60° C.; b. Et₂Zn, Pd(dppf)Cl₂, 1,4-dioxane, 65-70° C.; c. PhB(OH)₂, Pd(dppf)Cl₂, Cs₂CO₃, 1,4-dioxane, 70° C.

Example 1

Preparation of 3',4'-Anhydrovinblastine (A)

This compound was prepared from vinblastine sulfate (3.7 g, 4.1 mmol) according to a reported procedure with slight modifications (*Bull. Soc. Chim Belg.* 92:485 (1983), which is hereby incorporated by reference in its entirety). The crude product (3.0 g; a yellow solid) was used in the next step without purification: ESI MS m/z 793 [M+H]⁺.

Example 2

Preparation of 4'-Deoxy-20',20'-difluorovinblastine (B)

This compound was prepared from 3',4'-anhydrovinblastine (A; crude, 3.0 g) according to a reported procedure with slight modifications (U.S. Pat. No. 6,127,377, which is hereby incorporated by reference in its entirety), the spectral data of which were consistent with those reported therein (0.90 g, 26% over two steps).

Example 3

Preparation of 4'-Deoxy-20',20'-difluoro-12'-iodovinblastine (2)

4'-Deoxy-20',20'-difluorovinblastine (B; 300 mg, 0.36 mmol) was dissolved in MeCN (2 mL) and cooled to −15° C. Then conc. H₂SO₄ (0.30 mL) was added dropwise at −15° C. followed by dropwise addition of NIS (81 mg, 0.36 mmol) in MeCN (1 mL) at −10~−15° C. The reaction mixture was stirred at −15~−10° C. for 2 h, quenched with saturated NaHCO₃ (10 mL) and extracted with EtOAc (3×10 mL). The combined extracts were dried over Na₂SO₄, filtered, and concentrated to give the crude title compound as a brown-yellow solid, which was used in the next step without purification.

Example 4

Preparation of 4'-Deoxy-20',20'-difluoro-12'-methylthiovinblastine (12)

A mixture of 4'-deoxy-20',20'-difluoro-12'-iodovinblastine (2; crude, ca. 0.36 mmol), Et₃N (0.50 ml, 3.6 mmol) and Pd(dppf)Cl₂ (60 mg, 0.072 mmol) in NMP (4 mL) were degassed and purged with methanethiol three times. The reaction mixture was heated at 65° C. for 46 h. LC-MS analysis showed completion of the reaction. The reaction mixture was cooled to room temperature, diluted with EtOAc (15 mL) and washed with water (10 mL). The aqueous layer was extracted with EtOAc (2×10 mL). The combined organic layers were extracted with 0.5 N HCl (4×10 mL). The combined aqueous extracts were neutralized with NaHCO₃ and extracted with EtOAc (4×15 mL). The combined organic layers were dried over Na₂SO₄ and concentrated. The residue was purified by preparative HPLC. The pure fractions were combined and concentrated to dryness. The residue was partitioned between CH₂Cl₂/saturated aqueous NaHCO₃ (2 mL each). The aqueous layer was then extracted with CH₂Cl₂ (3×2 mL). The combined organic extracts were dried over Na₂SO₄ and concentrated to give the free base as a yellow solid (110 mg). This was converted to ditartrate salt and lyophilized to give the title compound as a white solid (117 mg, 27% over two steps): $^1$H NMR (500 MHz, D$_2$O) δ 9.48 (br s, 1H; partially exchanged), 7.49 (s, 1H), 7.25 (d, J=8.5 Hz, 1H), 7.15 (d, J=8.5 Hz, 1H), 6.58 (s, 1H), 6.39 (s, 1H), 5.90 (dd, J=10.4, 5.2 Hz, 1H), 5.60 (d, J=10.4 Hz, 1H), 5.24 (s, 1H), 4.46 (s, 4.4H), 3.89-3.70 (m, 4H), 3.81 (s, 3H), 3.78 (s, 3H), 3.73 (s, 1H), 3.65-3.54 (m, 4H), 3.61 (s, 3H), 3.44 (dd, J=17.5, 6.1 Hz, 1H), 3.35 (d, J=15.6 Hz, 1H), 3.29-3.20 (m, 2H), 3.12-3.11 (m, 1H), 2.98 (br d, J=9.2 Hz, 1H), 2.83-2.77 (m, 1H), 2.69 (s, 3H), 2.50-2.38 (m, 2H), 2.45 (s, 3H), 2.05 (s, 3H), 1.97 (br s, 1H), 1.77 (d, J=13.1 Hz, 1H), 1.65-1.48 (m, 6H), 1.33 (m, 1H), 0.62 (t, J=7.2 Hz, 3H); $^{13}$C NMR (125 MHz, D$_2$O) δ 176.3, 176.1, 172.8, 172.1, 158.6, 153.0, 133.9, 131.2, 130.2, 128.6, 127.4, 124.4 (t, J=240.3 Hz), 124.3, 123.0, 121.6, 120.3, 120.1, 117.5, 112.8, 112.4, 94.8, 79.9, 79.4, 74.8, 72.7, 66.5, 56.7, 56.0, 55.2, 53.7, 53.3, 52.0, 51.3, 49.5, 49.4, 45.9, 42.6, 42.3, 37.7, 35.0 (t, J=24.4 Hz), 34.1, 30.6, 27.4, 26.3, 20.9, 20.4 (t, J=26.6 Hz), 20.0, 17.9, 6.9; ES-MS: (M+H)=877 m/z; HPLC $t_R$=12.17 min, >99%. Calcd for C$_{47}$H$_{58}$F$_2$N$_4$O$_8$S.2.2C$_4$H$_6$O$_6$.2.5H$_2$O: <<Calcd>><<Found>>

Example 5

Preparation of 4'-Deoxy-20',20'-difluoro-12'-ethylvinblastine (3)

A mixture of 4'-deoxy-20',20'-difluoro-12'-iodovinblastine (2; crude, ca. 0.36 mmol), Et$_2$Zn (0.50 ml, 3.6 mmol) in 1,4-dioxane (5 mL) were degassed and purged with N$_2$ three times. Then, Pd(dppf)Cl$_2$ (60 mg, 0.072 mmol) was added and the reaction mixture was purged with N$_2$. The reaction mixture was heated at 80-90° C. for 6.5 h, cooled to room temperature, quenched with saturated aqueous NaHCO$_3$ (5 mL) and extracted with EtOAc (4×5 mL). The combined organic layers were dried over Na$_2$SO$_4$ and concentrated. The residue was purified by preparative HPLC and was converted to ditartrate salt as described for compound 5a above. Lyophilization gave the title compound as a white solid (54 mg, 12% over two steps): $^1$H NMR (500 MHz, D$_2$O) δ 9.39 (br s, 1H), 7.41 (s, 1H), 7.28 (d, J=8.4 Hz, 1H), 7.15 (d, J=8.4 Hz, 1H), 6.57 (s, 1H), 6.42 (s, 1H), 5.91 (dd, J=10.4, 4.4 Hz, 1H), 5.63 (d, J=10.4 Hz, 1H), 5.27 (s, 1H), 4.50 (s, 7.2H), 3.90-3.86 (m, 4H), 3.82 (s, 3H), 3.81 (s, 3H), 3.80-3.76 (m, 2H), 3.73 (s, 1H), 3.66 (s, 3H), 3.64-3.62 (m, 1H), 3.60-3.48 (m, 4H), 3.38 (br d, J=16.1 Hz, 1H), 3.32-3.22 (m, 2H), 3.13-3.07 (m, 1H), 3.00-2.96 (m, 1H), 2.86 (br s, 1H), 2.70 (s, 3H), 2.68-2.67 (m, 2H), 2.51 (br d, J=12.0 Hz, 1H), 2.43-2.37 (m, 1H), 2.07 (s, 3H), 2.02-1.94 (m, 1H), 1.82 (br d, J=13.2 Hz, 1H), 1.64 (t, J=19.7 Hz, 3H), 1.62-1.56 (m, 1H), 1.52-1.49 (m, 1H), 1.36-1.32 (m, 1H), 1.19 (t, J=7.6 Hz, 3H), 0.66 (t, J=7.2 Hz, 3H); ES-MS: (M+H)=859 m/z; HPLC $t_R$=12.17 min, 97.5%. Calcd for C$_{48}$H$_{60}$F$_2$N$_4$O$_8$S.3.6C$_4$H$_6$O$_6$.3H$_2$O: <<Calcd>><<Found>>

Example 6

Preparation of 4'-Deoxy-20',20'-difluoro-12'-phenylvinblastine (6)

A mixture of 4'-deoxy-20',20'-difluoro-12'-iodovinblastine (2; crude, ca. 0.38 mmol), PhB(OH)$_2$ (94 mg, 0.77 mmol) and Cs$_2$CO$_3$ (630 mg, 1.9 mmol) in 1,4-dioxane (10 mL) were degassed and purged with N$_2$ three times. Then Pd(dppf)Cl$_2$ (47 mg, 0.057 mmol) was added and the reaction mixture was purged with N$_2$. The reaction mixture was heated at 70° C. for 4 h, cooled to room temperature, poured onto ice (20 g), and extracted with EtOAc (4×15 mL). The combined organic layers were dried over Na$_2$SO$_4$ and concentrated. The residue was purified by preparative HPLC and was converted to ditartrate salt as described for compound 12 above. Lyophilization gave the title compound as a white solid (51 mg, 11% over two steps): $^1$H NMR (500 MHz, CD$_3$OD) δ 9.47 (br s, 1H; partially exchanged), 7.72 (s, 1H), 7.67-7.63 (m, 2H), 7.45-7.41 (m, 3H), 7.36 (d, J=8.4 Hz, 1H), 7.30 (t, J=7.3 Hz, 1H), 6.66 (s, 1H), 6.41 (s, 1H), 5.92 (dd, J=10.1, 4.4 Hz, 1H), 5.48 (d, J=10.1 Hz, 1H), 5.35 (s, 1H), 4.43 (s, 4.0H), 3.88 (s, 3H), 3.82 (s, 3H), 3.74 (s, 3H), 3.79-3.72 (m, 3H), 3.69-3.60 (m, 4H), 3.52-3.49 (m, 2H), 3.40 (t, J=14.7 Hz, 1H), 3.23-3.12 (m, 2H), 3.02-2.94 (m, 2H), 2.81-2.79 (m, 1H), 2.76 (s, 3H), 2.55 (br d, J=12.0 Hz, 1H), 2.25 (br s, 1H), 2.08 (s, 3H), 2.01-1.98 (m, 1H), 1.81 (br d, J=12.8 Hz, 1H), 1.73-1.65 (m, 5H), 1.50-1.44 (m, 2H), 1.32-1.28 (m, 1H), 0.80 (t, J=7.2 Hz, 3H); ES-MS: (M+H)=907 m/z; HPLC $t_R$=13.65 min, 98.6%. Calcd for C$_{52}$H$_{60}$F$_2$N$_4$O$_8$S.2C$_4$H$_6$O$_6$.2H$_2$O: <<Calcd>><<Found>>

Example 7

Description of Biological Assays

A. HeLa GI$_{50}$ Determinations

Growth inhibition (GI$_{50}$) values were measured on the human cervical carcinoma cell line, HeLa S-3, which were selected for growth on plastic. The HeLa cell assay was based on the description of Skehan et al., *J. Natl. Cancer Inst.*, 82:1107-12 (1990), which is hereby incorporated by reference in its entirety. HeLa cells were plated at 2×10$^4$ cells/well in 96 well plates. One day later, a control plate was fixed by the addition of TCA to 5%. After five rinses with tap water, the plate was air-dried and stored at 4° C. Test compounds were added to the remaining plates at 10-fold dilutions. Two days later, all plates were fixed as described above. Cells were then stained by the addition of 100 µL per well of 0.4% sulforhodamine B (SRB) in 1% acetic acid for 30 min at 4° C. Wells were then quickly rinsed 5× with 1% acetic acid and allowed to air dry. The SRB was then solubilized by the addition of 100 µL per well of unbuffered 10 mM Tris base. Dye was quantified by measuring absorbance at 490 nm on a Molecular Devices microplate reader. Growth inhibition was calculated according to the following equation: GI=100×(T−T$_0$)/(C−T$_0$), where the optical density (OD) of the test well after 2 days of treatment was T, the OD of the wells in the control plate on day 0 was T$_0$ and C was the OD of untreated wells. Plots of percent growth inhibition versus inhibitor concentration were used to determine the GI$_{50}$.

TABLE 2

Growth Inhibition (GI$_{50}$) of HeLa Cells for Compounds of the Current Invention.

| Example | HeLa Cells GI$_{50}$ (nM) |
| --- | --- |
| 3 | >1,000 |
| 6 | 23,060 |
| 12 | 93 |

Although the invention has been described in detail for the purpose of illustration, it is understood that such detail is solely for that purpose, and variations can be made therein by those skilled in the art without departing from the spirit and scope of the invention which is defined by the following claims.

What is claimed:
1. A compound of Formula (I) as follows:

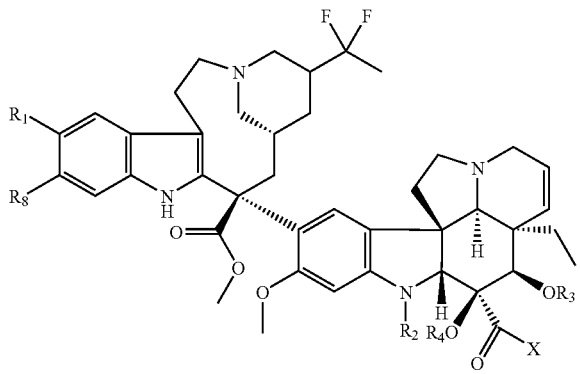

Formula I where:
R₁ is:
 alkenyl;
 alkynyl;
 aryl;
 heterocyclyl;
 halogen;
 CN;
 CH(O);
 COR₅;
 C(O)NR₅R₆;
 C(O)NHR₅;
 C(O)NH₂;
 C(O)NHNH₂;
 C(O)NR₅NH₂;
 C(O)NR₅NHR₆;
 C(O)NR₅NR₆R₇;
 C(O)NHNHR₅;
 C(O)NHNR₅R₆;
 C(O)NHOH;
 SO₂NHNH₂;
 SO₂NR₅NH₂;
 SO₂NR₅NHR₆;
 SO₂NR₅NR₆R₇;
 SO₂NHNHR₅;
 SO₂NHNR₅R₆;
 CO₂R₅;
 SR₅;
 SSR₅;
 SO₂NHR₅;
 SO₂NR₅R₆;
 B(OR₅)₂;
 CF₃;
 SH;
 SO₂NH₂;
 NH₂;
 NHR₅;
 NHSO₂R₅;
 NR₅R₆;
 NHCOR₅;
 NR₅COR₆; or
 NR₅SO₂R₆;
 SOR₅;
 SO₂R₅;
 OR₇; or R₂=alkyl or CH(O);
R₃=hydrogen, alkyl, or C(O)R₅;
R₄=hydrogen or C(O)R₅;
R₅, R₆, and R₇ each are independently hydrogen, alkyl, alkenyl, alkynyl, aryl, or heterocyclyl;
R₈=hydrogen, halogen, alkyl, alkenyl, alkynyl, aryl, heterocyclyl, acyl, or thioalkyl;
R₅ and R₆ could form a ring or R₆ and R₇ could form a ring;
X=OR₅, NR₅R₆, NHNH₂, NHNHC(O)R₅, OH, NHR₅, NH₂, or NHNHC(O)H;
R₄ and X may be linked together with intervening atoms to form a ring; R₁ and R₈ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

2. The compound according to claim 1, wherein R₃=acetyl.
3. The compound according to claim 1, wherein R₄=hydrogen.
4. The compound according to claim 1, wherein X=OMe.
5. The compound according to claim 1 wherein R₃=acetyl, R₄=hydrogen, and X=OMe.
6. The compound according to claim 1, wherein R₂=CH(O).
7. The compound according to claim 1, wherein R₂=alkyl.
8. A compound of Formula II as follows:

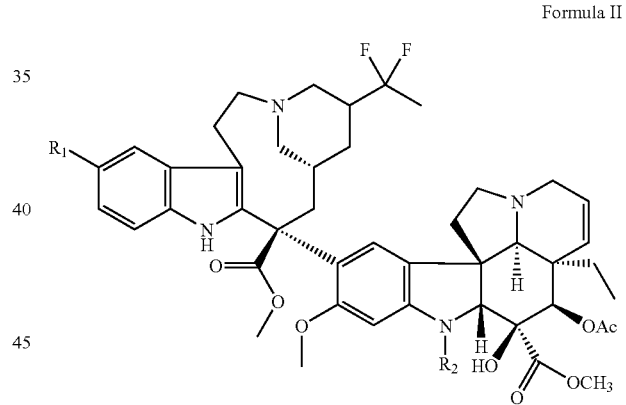

Formula II where:
R₁ is
 alkyl;
 alkenyl;
 alkynyl;
 CN;
 SR₅;
 CF₃;
 OR₇;
R₂=alkyl or CH(O);
R₅ and R₇ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

9. A compound of Formula III as follows:

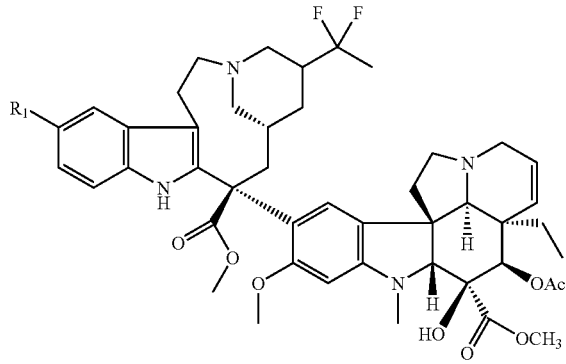

Formula III where:
R$_1$ is:
  SR$_5$;
  OR$_7$;
R$_5$ and R$_7$ are each independently hydrogen, alkyl, alkenyl, alkynyl, aryl, or heterocyclyl; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

10. A compound of Formula V as follows:

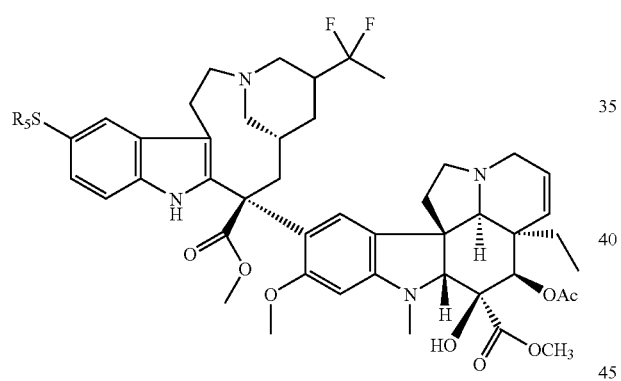

Formula V where:
R$_5$=alkyl; or a pharmaceutically acceptable salt thereof, wherein the alkyl group may be branched, straight, unsubstituted, and/or substituted.

11. The compound according to claim 10, herein the compound has the following chemical formula:

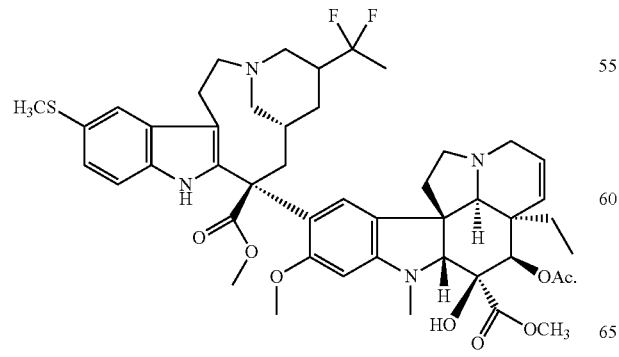

12. The compound according to claim 10, wherein the compound has the following chemical formula:

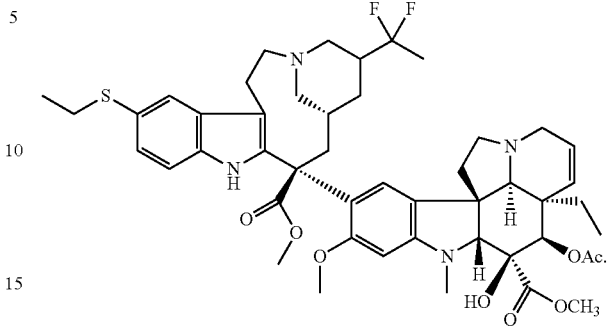

13. A process for preparation of a derivative product compound of Formula (I) as follows:

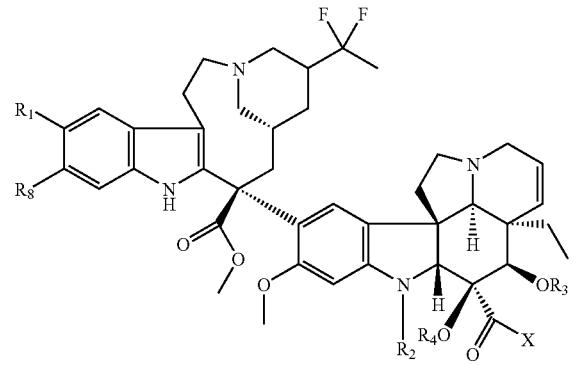

Formula I where:
R$_1$ is:
  alkyl;
  alkenyl;
  alkynyl;
  aryl;
  heterocyclyl;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;

SO$_2$NHR$_5$;
SO$_2$NR$_5$R$_6$;
B(OR$_5$)$_2$;
CF$_3$;
SH;
SO$_2$NH$_2$;
NH$_2$;
NHR$_5$;
NHCOR$_5$;
NHSO$_2$R$_5$;
NR$_5$R$_6$;
NHCOR$_5$;
NR$_5$COR$_6$; or
NR$_5$SO$_2$R$_6$;
SOR$_5$;
SO$_2$R$_5$;
OR$_7$; or

R$_2$=alkyl or CH(O);

R$_3$=hydrogen, alkyl, or C(O)R$_5$;

R$_4$=hydrogen or C(O)R$_5$;

R$_5$, R$_6$, and R$_7$ each are independently hydrogen, alkyl, alkenyl, alkynyl, aryl, or heterocyclyl;

R$_8$=hydrogen, halogen, alkyl, alkenyl, alkynyl, aryl, heterocyclyl, acyl, or thioalkyl;

R$_5$ and R$_6$ can form a ring or R$_6$ and R$_7$ can form a ring;

X=OR$_5$, NR$_5$R$_6$, NHNH$_2$, NHNHC(O)R$_5$, OH, NHR$_5$, NH$_2$, or NHNHC(O)H;

R$_4$ and X may be linked together with intervening atoms to form a ring; R$_1$ and R$_8$ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, said process comprising:

converting an intermediate compound of formula:

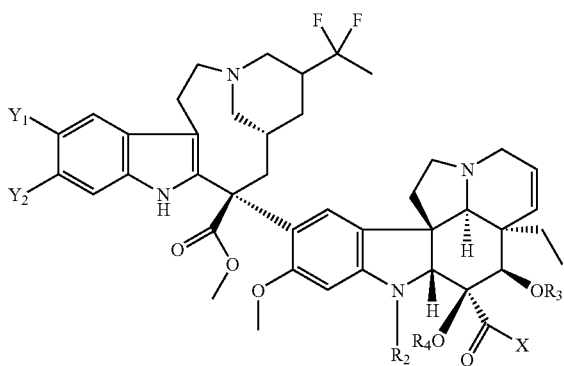

wherein Y$_1$ is a halogen and Y$_2$ is a halogen or hydrogen, under conditions effective to produce the product compound of Formula (I).

14. The process of claim 13 further comprising:
reacting a starting material compound of formula:

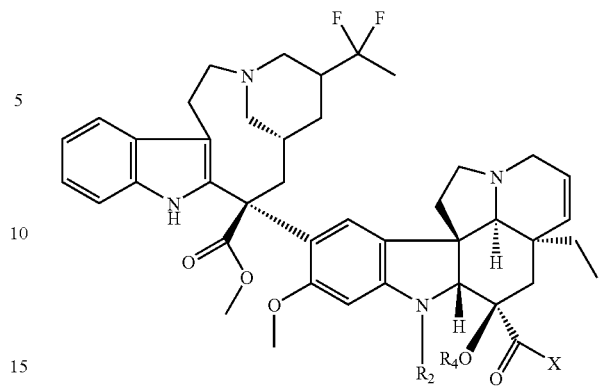

under conditions effective to form the intermediate compound.

15. The process of claim 14, wherein the conditions effective to form the intermediate compound include using a halogenating agent selected from the group consisting of N-bromosuccinimide, N-iodo-succinimide, and iodine monochloride.

16. The process of claim 14, wherein said converting comprises:
reacting the intermediate compound with a palladium catalyst reagent to produce the product of Formula (I).

17. The process of claim 16, wherein the palladium catalyst reagent is selected from the group consisting of palladium acetate, tris(dibenzylideneacetone)dipalladium(0), [1,1'-bis(diphenylphosphino)ferrocene]-dichloropalladium(II), tetrakis(triphenylphosphine)palladium, and bis(triphenylphosphine) palladium(II)dichloride.

18. A process for preparation of a derivative product compound of Formula (I) as follows:

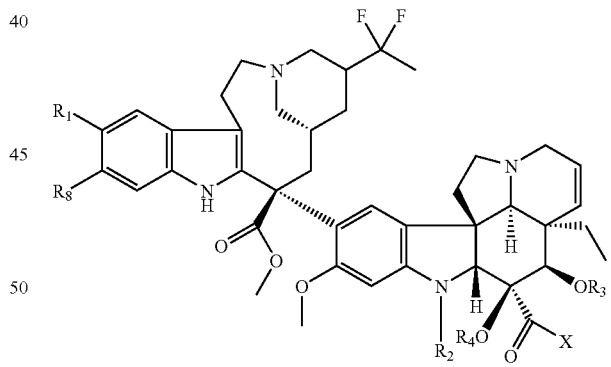

Formula I where:
R$_1$ is:
    halogen;
R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ can form a ring or R$_6$ and R$_7$ can form a ring;
X=OR$_5$, NR$_5$R$_6$, NHNH$_2$, NHNHC(O)R$_5$, OH, NHR$_5$, NH$_2$, or NHNHC(O)H;

R$_4$ and X may be linked together with intervening atoms to form a ring; R$_1$ and R$_8$ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, said process comprising:

reacting a starting material compound of formula:

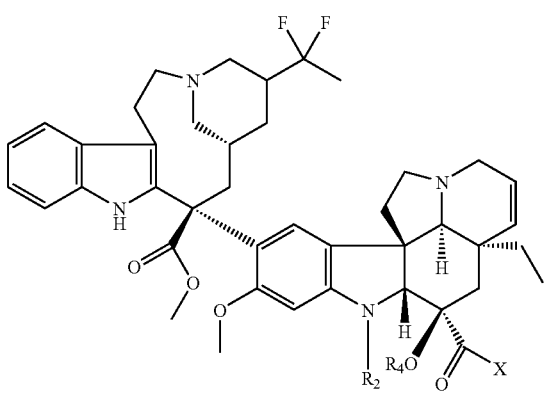

under conditions effective to form the derivative product compound.

19. The process of claim 18, wherein the conditions effective to form the intermediate compound include using a halogenating agent selected from the group consisting of N-bromosuccinimide, N-iodo-succinimide, and iodine monochloride.

20. A process for preparation of a derivative product compound of Formula (I) as follows:

Formula I

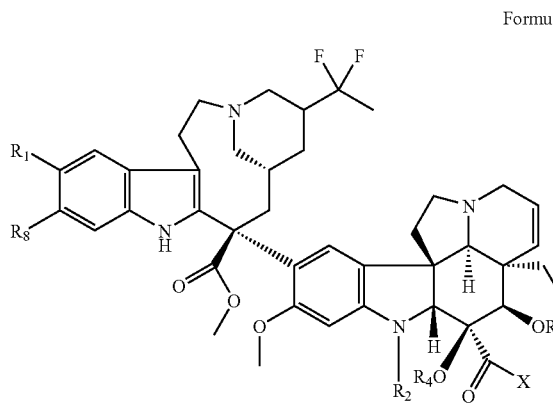

where:
R$_1$ is:
  alkenyl;
  alkynyl;
  aryl;
  heterocyclyl;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHCOR$_5$;
  NHSO$_2$R$_5$;
  NR$_5$R$_6$;
  NHCOR$_5$;
  NR$_5$COR$_6$;
  NR$_5$SO$_2$R$_6$;
  SOR$_5$;
  SO$_2$R$_5$; or
  OR$_7$;
R$_2$=alkyl or CH(O);
R$_3$=hydrogen, alkyl, or C(O)R$_5$;
R$_4$=hydrogen or C(O)R$_5$;
R$_5$, R$_6$, and R$_7$ each are independently hydrogen, alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_5$ and R$_6$ can form a ring or R$_6$ and R$_7$ can form a ring;
X=OR$_5$, NR$_5$R$_6$, NHNH$_2$, NHNHC(O)R$_5$, OH, NHR$_5$, NH$_2$, or NHNHC(O)H;
R$_4$ and X may be linked together with intervening atoms to form a ring; R$_1$ and R$_8$ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, said process comprising:

fluorinating an intermediate compound of formula:

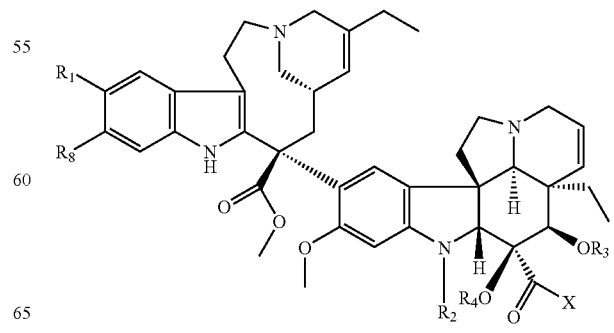

under conditions effective to produce the product compound of Formula (I).

21. The process of claim 13 further comprising:
converting a starting material compound of formula:

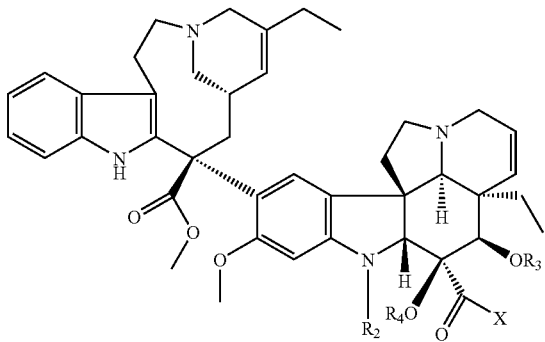

under conditions effective to form the intermediate compound.

22. The process of claim 21, wherein the conditions effective to form the intermediate compound include using a halogenating agent selected from the group consisting of N-bromosuccinimide, N-iodo-succinimide, and iodine monochloride.

23. A composition of matter comprising the compound of claim 1 and one or more pharmaceutical excipients.

24. The composition according to claim 23, wherein $R_3$=acetyl.

25. The composition according to claim 23, wherein $R_4$=hydrogen.

26. The composition according to claim 23, wherein X=OMe.

27. The composition according to claim 23, wherein $R_3$ acetyl, $R_4$=hydrogen, and X=OMe.

28. The composition according to claim 23, wherein $R_2$=CH(O).

29. The composition according to claim 23, wherein $R_2$=alkyl.

30. A method for treating a condition selected from the group consisting of breast cancer, Hodgkin's disease, and small cell lung cancer in mammals, said method comprising:
administering a therapeutically effective amount of the compound of claim 1 to the mammal.

31. The method according to claim 30, wherein $R_3$=acetyl.

32. The method according to claim 30, wherein $R_3$=acetyl, $R_4$=hydrogen, and X=OMe.

33. The method according to claim 30, wherein $R_2$=CH(O).

34. The method according to claim 30, wherein $R_2$=alkyl.

35. The method of claim 30, wherein the mammal is human.

36. A method for treating a condition selected from the group consisting of Non-Hodgkin's lymphoma, chronic myeloid leukemia, melanoma, squamous cell cervical cancer, and Kaposi's sarcoma in mammals, said method comprising:
administering a therapeutically effective amount of the compound of claim 1 to the mammal.

37. The method according to claim 36, wherein $R_3$=acetyl.

38. The method according to claim 36, wherein $R_3$=acetyl, $R_4$=hydrogen, and X=OMe.

39. The method according to claim 36, wherein $R_2$=CH(O).

40. The method according to claim 36, wherein $R_2$=alkyl.

41. The method of claim 36, wherein the mammal is human.

* * * * *

UNITED STATES PATENT AND TRADEMARK OFFICE
CERTIFICATE OF CORRECTION

PATENT NO. : 8,039,453 B2
APPLICATION NO. : 11/854186
DATED : October 18, 2011
INVENTOR(S) : Wolf et al.

It is certified that error appears in the above-identified patent and that said Letters Patent is hereby corrected as shown below:

Column 52, starting at line 1, delete "
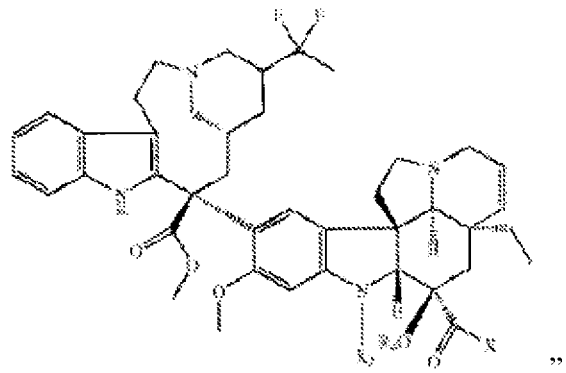
"

and insert --
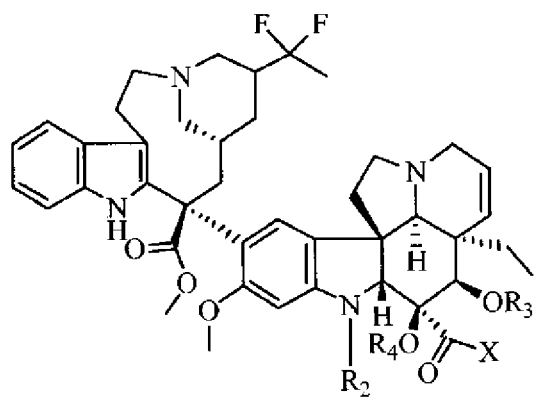
-- in its place.

Signed and Sealed this
Twenty-fifth Day of September, 2012

David J. Kappos
*Director of the United States Patent and Trademark Office*

CERTIFICATE OF CORRECTION (continued)
U.S. Pat. No. 8,039,453 B2

Column 53, starting at line 10, delete "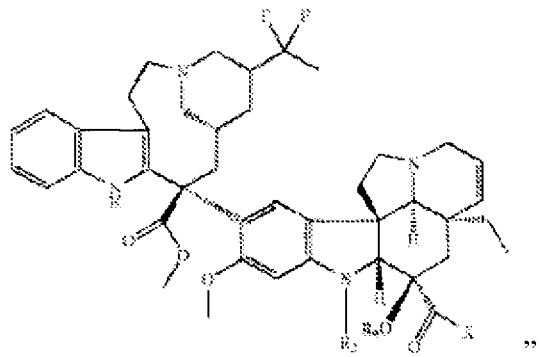"

and insert -- 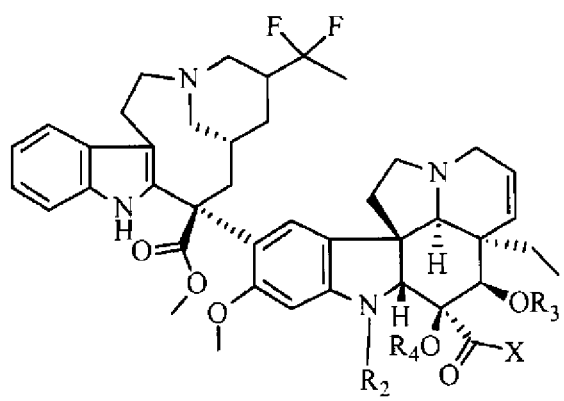 -- in its place.